United States Patent [19]

Yourno

[11] Patent Number: 5,432,097
[45] Date of Patent: Jul. 11, 1995

[54] METHOD FOR RECOVERY OF BLOOD CELLS FROM DRIED BLOOD SPOTS ON FILTER PAPER

[76] Inventor: Joseph Yourno, 1662 New Scotland Rd., Slingerlands, N.Y. 12159

[21] Appl. No.: 149,543

[22] Filed: Nov. 9, 1993

[51] Int. Cl.$^6$ .............................................. G01N 1/00
[52] U.S. Cl. ...................... 436/175; 436/63; 436/174; 436/178; 435/2; 422/56; 128/760
[58] Field of Search ................. 436/63, 164, 174, 175, 436/177, 178; 435/2; 422/61, 56; 128/760

[56] References Cited

U.S. PATENT DOCUMENTS

| | | | |
|---|---|---|---|
| 3,904,781 | 9/1975 | Henry | 427/2 |
| 4,066,359 | 1/1978 | Bucalo | 356/36 |
| 4,106,989 | 8/1978 | Komura et al. | 435/209 |
| 4,299,812 | 11/1981 | Coombes | 436/500 |
| 4,431,743 | 2/1984 | Pang et al. | 436/542 |
| 4,943,532 | 7/1990 | Kawai et al. | 435/209 |
| 4,950,455 | 8/1990 | Smith | 422/56 |
| 5,141,643 | 8/1992 | Breitbach et al. | 210/503 |
| 5,204,267 | 4/1993 | Sangha et al. | 436/14 |
| 5,250,438 | 10/1993 | Ryan | 436/17 |
| 5,252,489 | 10/1993 | Macri | 436/87 |

OTHER PUBLICATIONS

Yourno et al. Journal of Clinical Microbiology, vol. 30, No. 11, Nov. 1992, pp. 2887–2892.
Condensed Chemical Dictionary–10th edition, 1981 p. 209.
Routine Cytological Staining Techniques, 1986, pp. 113–114.
Hematology: Principles and Procedures,-3rd edition, 1980, pp. 75–76.

*Primary Examiner*—James C. Housel
*Assistant Examiner*—Maureen M. Wallenhorst
*Attorney, Agent, or Firm*—Schmeiser, Olsen & Watts

[57] ABSTRACT

White blood cells (WBC) were recovered from dried blood spots on Guthrie cards by a simple and efficient prototypic method. The mummified formed elements of dried blood on filter paper are first fixed, then the red blood cells laked in-situ. Last, the paper matrix is itself digested away with cellulase in acid buffer, releasing the partially rehydrated, mummified WBC and other cellular materials into suspension for collection and examination.

8 Claims, 3 Drawing Sheets

METHOD FOR RECOVERY OF BLOOD CELLS FROM DRIED BLOOD SPOTS ON FILTER PAPER

FIELD OF THE INVENTION

The present invention relates to a method and apparatus for recovery of blood cells from dried blood on filter paper for diagnostic and research tests.

BACKGROUND OF THE INVENTION

The testing of blood samples in mass screening programs (e.g., testing performed on newborns and individuals remote from the testing center) has introduced a need for greater preservation time of blood samples in a more efficient manner before many types of lab tests can be performed. Currently, blood is preserved through two methods for microscopic or cytometric examination of cells or formed elements. In the first method, blood is preserved in a dry form by spotting on glass slides. The second method includes preservation of wet blood in packages (e.g. in test tubes) having anticoagulant therein. The difficulty with preserving dry blood on glass slides is the blood spot on each glass slide is generally limited to a single testing procedure. Once the blood is spotted on the slide, it cannot be transferred to another slide to perform further microscopic examinations. When a large number of individuals are being tested, this complicates the testing in that each slide needs to be carefully labelled and arranged for indexing. Also, the weight for storage and shipping becomes costly for a large number of glass slides.

The main difficulty with wet blood-in anticoagulant is the limited preservation time before the blood cells begin to fall apart (e.g., through hemolysis or pyknosis). The preservation time of wet blood is generally twenty-four (24) hours for microscopic testing. In mass central screening programs a greater time span than twenty-four hours is desirable for shipping and storage. For example, if a United States lab was being used for mass central screening of blood from Africa or Southeast Asia for Acquired Immunodeficiency Syndrome (AIDS), cells in wet blood samples would fall apart and be unusable for microscopic cell-based testing by the time they reached the lab. Another area with similar concerns in which mass screening of preserved blood is used is with newborns for detection of inherited conditions/disorders.

SUMMARY OF THE INVENTION

The present invention solves the difficulties of the prior art by providing a method and apparatus for analysis of dried blood collected from blood spots on filter paper (e.g., Guthrie cards) (See Guthrie R., *Blood Screening for phenylketonuria,* JAMA 1961;178:863, which is hereby incorporated by reference. Preserving blood cells on filter paper provides an advantage over glass slides in that filter paper is lighter and less bulky for indexing, storage and transportation. Also, the dried blood on a single spot on the filter paper may be made into a plurality of slides after the filter paper has been degraded. The present invention also overcomes the problems with wet blood in that the dried blood on filter paper increases the shelf life of the preserved blood.

The present invention provides a method and apparatus for molecular diagnostics of blood cells on filter paper, such as the polymerase chain reaction (PCR) for use in applications such as genetic screening (See Seltzer, et al., *Screening for cystic fibrosis: Feasibility of molecular genetic analysis of dried blood specimens,* Biochem Med and Metab Biol 1991;46:105 which is hereby incorporated by reference) and for infectious diseases screening. (See Cassol et al., *Diagnosis of vertical HIV-1* transmission using the polymerase chain reaction and dried blood spot specimens, J Acquir Immune Def Syndr 1992;5:113; Comeau et al., Detection of HIV in specimens from newborn screening programs, N Engl J Med 1992;320:1703.6; and Yourno et al., A novel polymerase chain reaction method for detection of human immunodeficiency virus in dried blood spots on filter paper, J Clin Microbiol 1992; 30:2a887, which are all hereby incorporated by reference.). More generally, similar analysis of pediatric or adult blood collected far afield from the testing site may be expedited when specimens are dried on filter paper. Microscopic examination of formed elements recovered from dried blood has not been attempted in the past, presumably because these elements have been considered beyond salvage, whether due to irreversible degradation in-situ or binding to the paper matrix. Contrary to this presumption, mummified white blood cells (WBC) can be recovered from dried blood spots on filter paper such as Guthrie cards.

The present invention is expected to have great utility and application in development of tests on white blood cells (WBCs) such as in-situ molecular analyses; morphologic or other type of enumeration of cells; and recovery of red blood cells and platelets from dried blood on filter paper for microscopic tests. In general, its applicability is expected to include molecular, quantitative, and enumertative hematology. Some specific projected applications include:

(1) detection of infectious agents in newborn, pediatric, or adult WBC by in-situ hybridization or PCR (e.g. Human Immunodeficiency Virus (HIV), Human T-cell Lymphotropic Virus (HTLV), Cytomeglovirus (CMV)).

(2) detection of leukemic WBC or tumor cells in blood or other tissues by in-situ molecular techniques.

(3) WBC count and differential counts for numerous infectious diseases, inflammatory states, leukocytosis or leukocytopenias.

(4) detection of maternal WBC in cord blood or newborn blood by in-situ molecular techniques.

In summary, the invention is expected to be applicable to the same range of microscopic testing or cytometric examination that wet blood is applicable to.

DETAILED DESCRIPTION OF THE PREFERRED EMBODIMENT(S)

Principle

Figure 1:
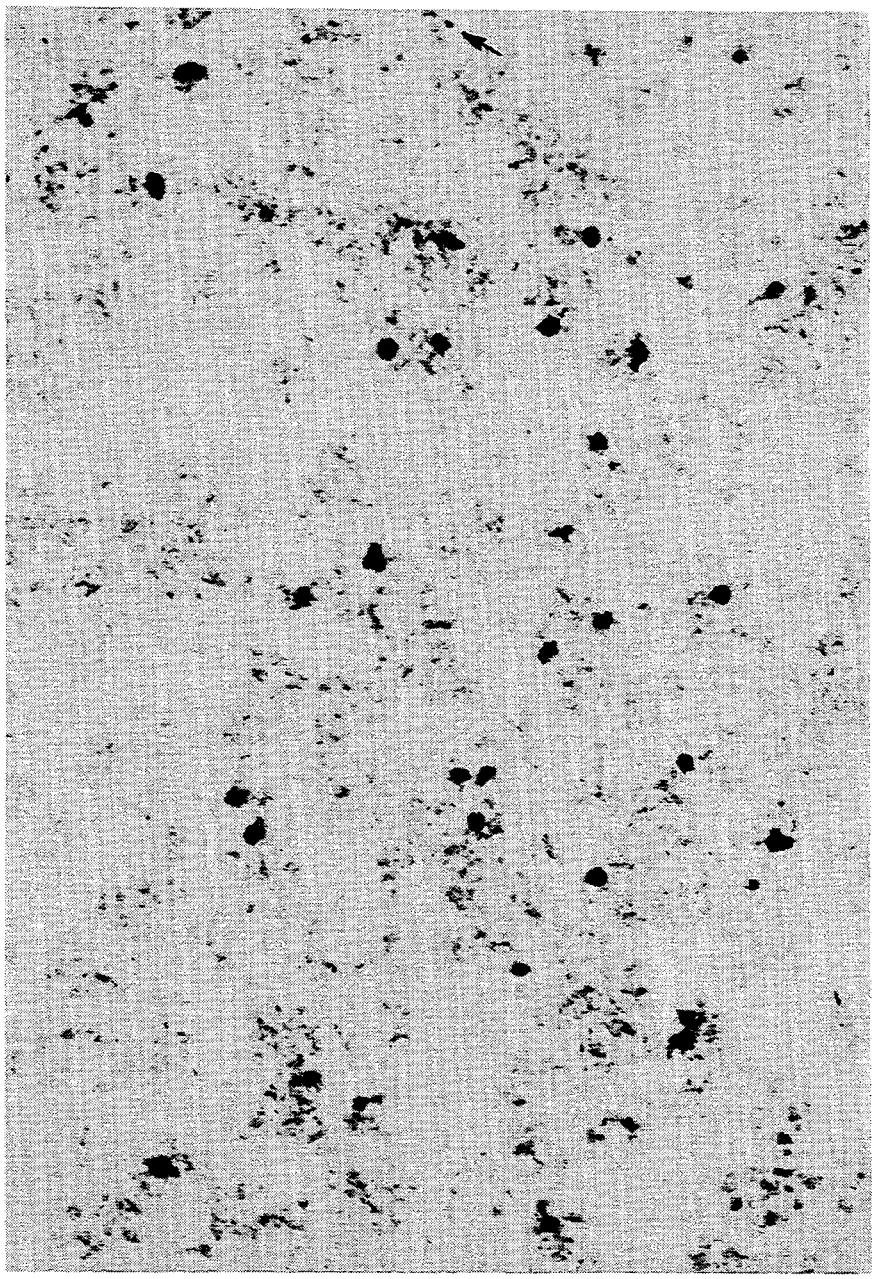
FIG. 1 represents Wright's stained slide preparations of partially rehydrated, mummified WBCs recovered from dried blood spots from whole blood source with 5700 WBC/$\mu$L using Kodak Pan-X, ASA100 at 100× magnification. See Table I for further details.

The mummified formed elements of dried blood on filter paper are first fixed in-situ to maintain the bodily integrity of the WBC through storage and subsequent isolation. Red blood cells (RBC) are next laked in-situ to reduce RBC background, leaving the fixed WBC and RBC ghosts adherent to the paper matrix. Last, the paper matrix is itself digested away with cellulase in acid buffer, releasing the partially rehydrated, mummified WBC and other cellular materials into suspension for collection and examination.

Blood spot materials

Blood spot specimens were prepared on Guthrie cards (See Yourno et al, *supra,* which is hereby incorporated by reference) from a normal donor WBC concentrate (buffy coat) anticoagulated in acid-citrate-dextrose and from seven normal donor whole bloods anticoagulated in ethylenediaminetetraacetic acid. WBC counts were performed by hemacytometer on 10× dilutions of each anticoagulated blood source in 2% acetic acid (Nelson, D, *Basic examination of the blood,* In: Henry JB, ed. Clinical diagnosis and management by laboratory methods, 18th edition, Philadelphia: W. B. Saunders Co., 1991:564, which is hereby incorporated by reference) (duplicate grids, 2×0.1 mm³ fields counted in each). Counts ranged from low to high normal in whole bloods to markedly elevated in the WBC concentrate (reference interval, 4500–11000 WBC/µL (See Nelson, supra)) (See Table I). WBC differential counts were made on Wright's stained blood smears (Quick Stain procedure, 100–200 cell counts). All specimens yielded differential counts within the reference interval (See Nelson supra) (granulocytes, 58–78%; lymphocytes, 21–40%; monocytes, 2–10%). Blood spots of ½ in diameter (equivalent to 50 µL blood) were prepared dropwise onto Guthrie cards with a serological pipette and air-dried 2–4 h at room temperature. The cards were stored in plastic bags at 4°–8° C.

Fixation and lysis steps.

After 24-h storage in each case, the filter paper strips with dried blood spots ×5 were cut from the cards, immersed in 60 mL absolute acetone for 10 min at room temperature, air-dried for 10–20 min at room temperature, and stored over drierite in a 1-L roller bottle at 4°–8° C. After storage for 24 h (normal whole bloods) to 5½ months (WBC concentrate), the treated strips were immersed lengthwise in an upright centrifuge tube containing 55 mL 2% acetic acid for 3 h at room temperature to lake the RBC. The RBC is burst, releasing the hemoglobin and leaving only the empty red cell membrane on the paper (RBC's contain no nucleus, only cytoplasm rich in hemoglobin which is enclosed in a cell membrane. The hemoglobin released from the disrupted RBC formed a loose sediment at the tube bottom over this time, leaving each blood spot residue a light reddish-brown. The doubly-treated strips were then air dried for 2–4 h at room temperature and stored as above.

TABLE 1

Recovery of WBC from dried blood spots on Guthrie cards; hemacytometer counts.

| Anticoagulated source blood starting WBC | | Dried filter paper specimen WBC recovered | | | WBC left | |
|---|---|---|---|---|---|---|
| WBC count/µL[a] X ± S.D. | WBC count/12 µL X | | WBC count[b] X ± S.D. | % X ± C.V. | WBC count[c] X | % X |
| Whole blood | | | | | | |
| (1) 5729 ± 426 | 68748 | A | 57420 ± 9811 | 84 ± 14 | 183 | 0.3 |
| | | B | 56100 ± 9714 | 82 ± 14 | 183 | 0.3 |
| (2) 5804 ± 668 | 69648 | A | 69300 ± 11016 | 100 ± 16 | | |
| | | B | 66825 ± 8775 | 96 ± 13 | | |
| (3) 6583 ± 920 | 78996 | A | 73838 ± 19478 | 93 ± 26 | | |
| | | B | 58163 ± 13299 | 74 ± 23 | | |
| (4) 6559 ± 421 | 78708 | A | 54038 ± 20625 | 69 ± 26 | | |
| | | B | 51975 ± 14190 | 66 ± 18 | | |
| (5) 8316 ± 459 | 99792 | A | 94600 ± 31900 | 95 ± 32 | 367 | 0.4 |
| | | B | 84150 ± 17886 | 84 ± 18 | 550 | 0.6 |
| (6) 4673 ± 535 | 56076 | A | 38775 ± 3160[a] | 69 ± 6 | 550 | 1.0 |
| | | B | 41250 ± 19503[a] | 74 ± 35 | 367 | 0.7 |
| (7) 5603 ± 405 | 67236 | A | 53213 ± 16208 | 79 ± 24 | | |
| | | B | 51563 ± 10276 | 77 ± 15 | | |
| WBC concentrate | | | | | | |
| 51577 ± 2445 | 618924 | A | 532950 ± 39278[a] | 86 ± 6 | 2750 | 0.4 |
| | | B | 505730 ± 13303[a] | 82 ± 2 | 4216 | 0.7 |
| | | | | Overall X ± C.V. 82 ± 10 | X 0.4 | |

[a] 2 × 0.1 mm³ fields each counted in duplicate grids,
[b] 4 × 0.1 mm³ fields each counted in duplicate grids except as noted.
[c] Count over entire grid.

Cellulase digestion

After storage for 24 h, filter circles were punched from the blood spots with a ¼ inch paper punch and duplicate circles from each blood spot specimen were transferred each into a 1.5-mL gasketed screw-cap tube (Sarstedt). A solution of Penicillium cellulase (Sigma) was freshly prepared at a concentration of 10 mg/mL of isotonic phosphate buffered saline, pH 5 (PBS.5). To prepare PBS.5, a 25-mL solution of standard PBS, pH 7, was brought to pH 5 by addition of 2.0 g $KH_2PO_4$, then restored to isotonicity by 4× dilution with distilled water. The fresh cellulase preparation was filtered through a 22-µm nitrocellulose filter to remove insoluble debris and 1.0-mL aliquots of the clear, light yellow solution were added to each digestion tube containing a filter circle. The filter circles were then digested for 2 h at 37° at 100–150 rpm on a continuous action vortexer (Vortex Genie II). The end point of the digestion was evidenced by complete disintegration of the filter circle into a coarse, fluffy suspension.

Recovery of WBC

The digests were allowed to settle 5–10 min at room temperature. The pale yellow supernatant and loose reddish-green upper layer of sediment were aspirated from the compacted white paper underlayer and transferred to a graduated 15-mL screw-cap test tube. The digest pellet was twice resuspended in 1.0 mL PBS.5, and resedimented as above. Aspirates from the resedimentations were combined with the original in the 15-mL tube. This suspension (3 mL) was centrifuged at $1250 \times g$ for 10 min at room temperature in a swinging-bucket centrifuge (International CRU-5000). The clear supernatant was aspirated off to the 0.3 mL mark and the pellet resuspended in residual buffer. A 100-$\mu$L aliquot of this suspension was mixed with 10 $\mu$L of Wright's stain (Quick Stain solution 3) for cell counts and for preparation of slide buttons on glass slides. All fractions including the paper residue were stored at 4° C.

Cell counts and microscopy of rehydrated WBC in wet mounts

After 24-h storage of WBC suspensions at 4° C., direct hemacytometer counts of each were made with duplicate grids, where four fields each were scored. The calculated recovery of WBCs ranged from 66 to 100%, based on an equivalent of 12 $\mu$L anticoagulated source blood per filter circle (See Table I). The dilute suspensions from whole blood (equivalent to 12 $\mu$L blood in 330 $\mu$L final volume, i.e., $27.5 \times$ dilution) yielded expectedly high coefficients of variation ranging from 6 to 35%). The suspensions from the WBC concentrate gave less variation at equivalent dilution (2 and 6%). An aliquot of the paper residue from selected preparations was likewise examined by hemacytometer scan as a wet squash mount. Rare WBC, fewer than 1% of the calculated starting count in each case, remained within the mass of paper fibers (See Table I).

Morphologically, the wet hemacytometer mounts showed mummified WBC with moderately stained basophilic nuclei, surrounded by a thin, lightly staining, clear to granular rim of shrunken cytoplasm and cell membrane, which was visible more by phase contrast than by staining ($400 \times$).

Figure 2:
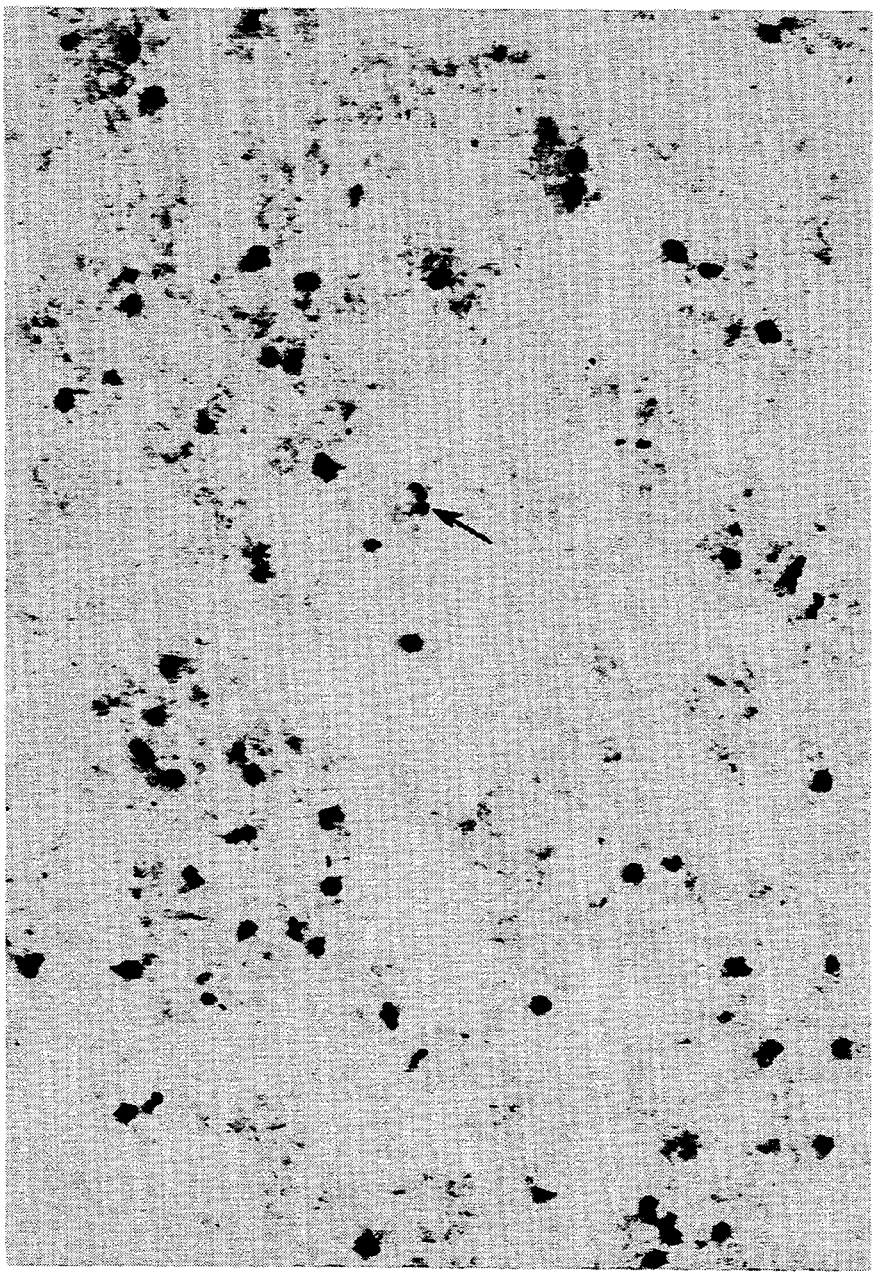
FIG. 2 is substantially the same as FIG. 1 except that the dried blood spots are from whole blood source with 8300 WBC/$\mu$L.
Figure 3:
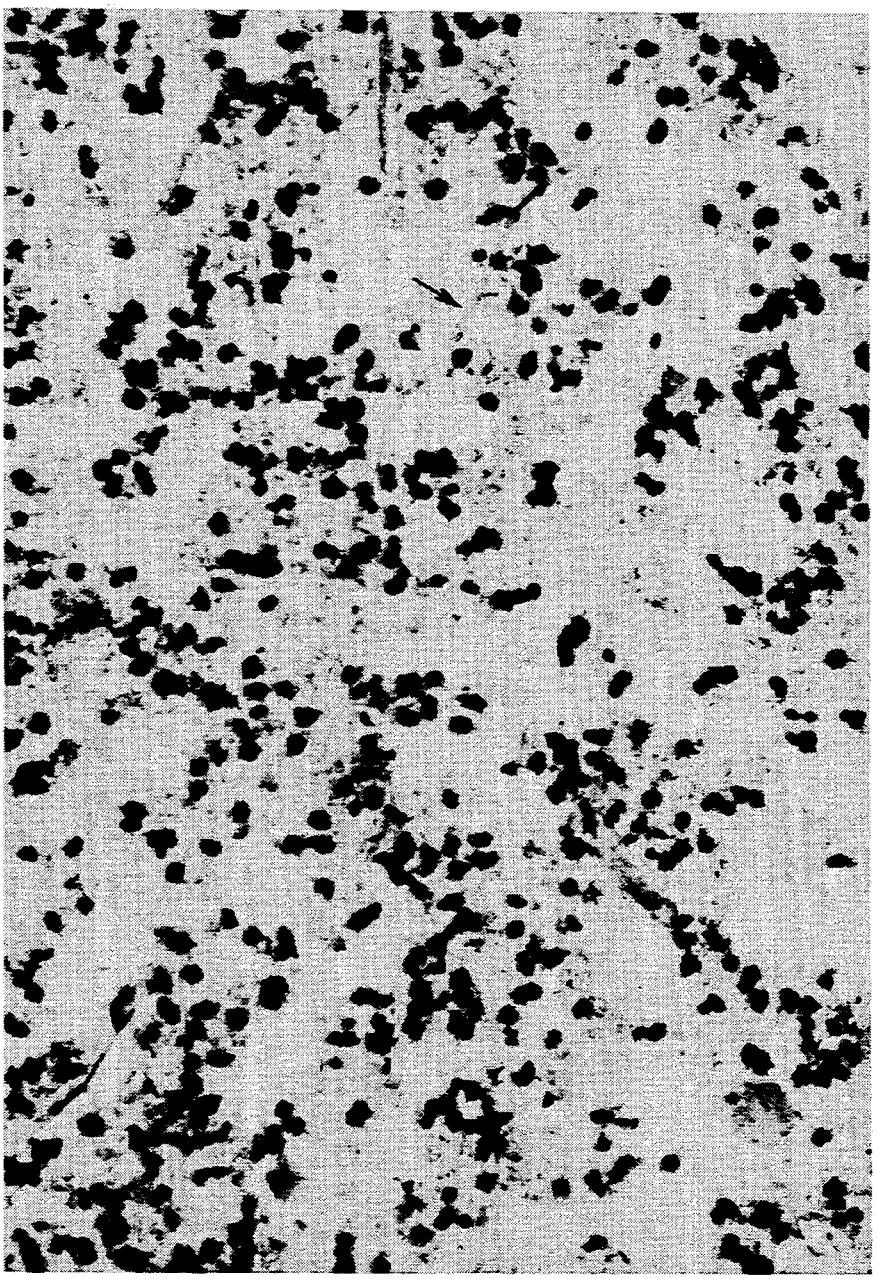
FIG. 3 is substantially the same as FIG. 1 except that the dried blood spots are from WBC concentrate with 51,600 WBC/$\mu$L.

The recovered WBC ranged from an estimated 7 to 15 $\mu$m in diameter. Nuclear detail of the differentiation of granulocytes from mononuclear cells is expected to be greatly enhanced. Occasional WBC with outstretched, segmented nuclei were reminiscent of granulocytes. As seen in FIGS. 1–3, mummified WBC with moderate to deep stained nuclei are visualized against a background of granular RBC debris. The thin rim of lightly stained, shrunken cytoplasm and cell membrane around the WBC nucleus is not seen. The arrow in FIG. 1 shows apparent granulocytes, each with outstretched segmented nucleus. The arrow in FIG. 2 shows cell fragments. The arrow in FIG. 3 indicates occasional cellulose (paper) fiber. Basophilic cell fragments an estimated 2–4 $\mu$m in diameter, not counted as WBC, comprised up to 5% of the WBC count in about half the preparations; in the remaining these ranged from 7–15% of the WBC count. Some cells showed outstretched nuclear lobes connected by a thin bridge. These are a likely origin of the cell fragments, reflecting some pyknotic change during isolation. A background of lightly staining RBC debris was present in each wet mount, as well as occasional residual paper fibers. These did not interfere with cell counts and morphologic examination.

Microscopic examination of recovered WBC by Wright's stain

From the same suspensions used for cell counts and wet mounts, 5-$\mu$L aliquots of each specimen were spotted onto a glass slide, air-dried, refixed in methanol for 1–2 min, stained in eosinophilic stain for 60 min, and then in Wright's stain for 60 min (Quick Stain solutions 1, 2, and 3 respectively). Prolonged staining was found better to visualize the partially rehydrated, mummified WBC. Microscopic examination of these slide button preparations showed a picture similar to that of wet mounts, but the thin rim of shrunken cytoplasm and cell membrane surrounding the WBC nucleus was not evident, even under oil immersion ($1000 \times$). (See FIGS. 1–3).

Discussion

The method described for recovery of partially rehydrated, mummified WBCs from dried blood spots on Guthrie cards has been developed empirically. When unfixed filter circles containing dried WBC concentrate were rehydrated and teased apart in Hank's medium, pH 7, only rare free WBC were recovered, but Wright's stained buttons of the paper macerates on glass slides, encouragingly, revealed abundant WBC remnants trapped in the paper fibers. To release the WBC from the paper, the strategy was adopted to destroy the paper substratum with cellulase. Fungal cellulase showed poor activity when filter circles were treated at physiological pH in Hank's medium. The cellulase, which has a pH optimum around pH 5, readily digested the paper matrix at pH 5, however, and released the trapped WBC into suspension. For improved preservation of WBC through storage and isolation from filter circles, dried blood spots were fixed in-situ on the filter paper. Several fixatives were assessed. On the one hand, "hard" fixatives such as methanol yield sharply stained, well preserved WBC mummies, but also cause troublesome clumping of WBC and RBC. On the other hand, "softer" fixatives such as acetone yield WBC which are more hydrated and lightly staining, but clumping is largely eliminated. Unfixed blood spots on Guthrie cards, stored at 4°–8° C. without drying agent and warmed to room temperature numerous times, showed acceptable WBC preservation over a 4 month period from preparation. When next checked at 18 months, however, significant degeneration was evident. Acetone-fixed blood spots have shown good WBC preservation up to 9 months of storage over drierite. Longevity of these fixed preparations is probably much greater than this last measured time span.

Several methods for RBC lysis were tried to eliminate the overwhelming RBC background in cellulase digests of filters. A simple solution of 2% acetic acid produces excellent results. While the protocol which has been devised gives efficient recovery of partially rehydrated, mummified WBC, cell morphology is not sufficiently preserved for differential counts. It is not yet clear whether this is the irreversible result of blood desiccation on the filter paper (instead of on a flat slide) or of the nonphysiological isolation procedure itself.

When WBC suspensions produced by cellulase digestion of filter circles were brought back to pH 7 in PBS, lysis of WBC resulted. It remains to be determined whether accurate differential counts can be developed for recovered WBC, by morphologic or other criteria. Further modifications of the procedure are expected to improve cellular integrity and morphology, viz., use of purified cellulase, gentler agitation and/or ambient temperature for digestion. A few neutral cellulases have been described (See Yamane et al., *Cellulases of Psuedomonas fluorescens var. cellulos,* In: WA Wood and ST Kellogg, eds. Methods Enzymol, Vol. 160. San Diego: Academic Press, 1988:200, which is hereby incorporated by reference) which may permit recovery of WBC in unmodified physiological buffers. This prototype study was based on workup of anticoagulated bloods. As such it is directly applicable to screening procedures using this starting material. It should be extended to bloods prepared from skin punctures directly onto filter paper, possibly impregnated with anticoagulant as an easy way to deal with potential blood clotting problems.

These results are expected to have application to diverse tests on WBC recovered from dried blood spots, from WBC counts to more complex analyses such as in-situ hybridization and PCR. Finally, the results encourage evaluation of variations on the basic procedure to retrieve the other formed elements (e.g., red blood cells and platelets) from dried blood.

I claim:

1. A method for recovery of blood cells from dried blood on a degradable cellulosic medium comprising:
   providing a degradable cellulosic medium;
   placing blood cells on said degradable cellulosic medium;
   allowing said blood cells to dry;
   fixing said dried blood cells on said cellulosic medium;
   degrading said medium with an enzyme specific for said degradable cellulosic medium in a buffer; and
   releasing intact blood cells into a suspension for subsequent analysis wherein said intact blood cells contain at least a cell membrane and cytoplasm.

2. The method of claim 1, wherein said intact blood cells are white blood cells (WBC).

3. The method of claim 2, before the step of degrading, including the further step of:
   laking red blood cells (RBC) to reduce RBC background on said medium.

4. The method of claim 3, wherein said medium is paper.

5. The method of claim 4, wherein the step of degrading further comprises:
   degrading said medium with cellulase in an acid buffer, thereby releasing the intact blood cells into said suspension.

6. The method of claim 1, further comprising after the step of releasing:
   spotting said intact blood cells on a slide.

7. A method for recovery of intact white blood cells from cellulosic filter paper comprising:
   providing dried white blood cells on cellulosic filter paper;
   fixing said dried white blood cells on said filter paper;
   degrading said filter paper using cellulase in acid buffer; and
   releasing intact white blood cells into a suspension for subsequent analysis of the intact white blood cells wherein said intact white blood cells contain at least a cell membrane and cytoplasm.

8. The method of claim 7, before the step of degrading, including the further step of:
   laking red blood cells (RBC) to reduce the RBC background on said cellulosic filter paper.

* * * * *